United States Patent [19]

Lo et al.

[11] Patent Number: 5,639,710

[45] Date of Patent: Jun. 17, 1997

[54] SOLID MICROSPHERES FOR AGRICULTURALLY ACTIVE COMPOUNDS AND PROCESS FOR THEIR PRODUCTION

[75] Inventors: Ray Jia Lo, San Leandro; Ernesto Noe Villafranca, Oakland, both of Calif.

[73] Assignee: Zeneca Limited, London, Great Britain

[21] Appl. No.: 271,298

[22] Filed: Jul. 6, 1994

[51] Int. Cl.$^6$ .................................................. A01N 25/28
[52] U.S. Cl. ............... 504/116; 71/DIG. 1; 424/405; 424/497; 514/521; 514/963
[58] Field of Search ........................ 424/405, 497; 514/521, 963; 504/206, 116; 71/DIG. 1; A01N 25/28

[56] References Cited

U.S. PATENT DOCUMENTS

| | | | |
|---|---|---|---|
| 3,746,621 | 7/1973 | Kondo | 195/63 |
| 4,122,192 | 10/1978 | Fellows | 424/333 |
| 4,244,836 | 1/1981 | Frehsch et al. | 252/316 |
| 4,534,784 | 8/1985 | Ahle | 71/87 |
| 5,073,191 | 12/1991 | Misselbrook et al. | 71/DIG. 1 |
| 5,201,925 | 4/1993 | Itzel et al. | 47/58 |
| 5,354,742 | 10/1994 | Deming et al. | 514/117 |

FOREIGN PATENT DOCUMENTS

| | | |
|---|---|---|
| 12836/92 | 9/1992 | Australia . |
| 380325 | 8/1990 | European Pat. Off. . |
| 525333 | 6/1991 | European Pat. Off. . |
| 508155 | 10/1992 | European Pat. Off. . |
| 548901 | 6/1993 | European Pat. Off. . |
| 53-50333 | 8/1978 | Japan . |
| 53-138736 | 12/1978 | Japan . |
| 63-5003 | 1/1988 | Japan . |
| 2013610 | 8/1979 | United Kingdom . |
| 91/17821 | 11/1991 | WIPO . |

*Primary Examiner*—S. Mark Clardy
*Attorney, Agent, or Firm*—Joel G. Ackerman

[57] ABSTRACT

Microspheres containing an agriculturally active material are produced by mixing a liquid phase containing the agriculturally active material and optionally an emulsifying agent and an aqueous phase containing polyvinyl alcohol and adding a material selected from clays, silicas, starch, and starch derivatives, followed by spray drying.

20 Claims, No Drawings

SOLID MICROSPHERES FOR AGRICULTURALLY ACTIVE COMPOUNDS AND PROCESS FOR THEIR PRODUCTION

BACKGROUND AND PRIOR ART

This invention relates to the production of solid microspheres for use in controlled release of agriculturally active materials, particularly liquid materials.

There are a number of techniques available in the art for providing controlled-release formulations of such materials. Among those are procedures for encapsulating compounds in shells comprised of various polymers. The capsules may contain the agriculturally active materials in various physical forms. In some processes the capsules are formed by producing an emulsion of a liquid active ingredient (which may be in the form of the ingredient per se in liquid form or a solution of it in an appropriate solvent) in a second phase in the presence of one or more monomers or pre-polymers followed by processing steps to produce a shell of a polymer surrounding the emulsified droplets of active liquid material. In other embodiments, the active liquid ingredient may be present as an emulsion, in a solution, or as a suspension of smaller microspheres, within the capsule formed by the polymer.

One technique for producing controlled release formulations in the form of microspheres involves dispersing a liquid, water-insoluble active ingredient (which may be the ingredient per se or a solution of it in a water-immiscible solvent) in an aqueous phase containing polyvinyl alcohol, and then forming the microcapsules or microspheres by spray-drying this dispersion to remove the solvent and the water. Such a process is disclosed in general, in U.S. Pat. No. 4,244,836 of Frensch et al.

Modifications or improvements of this process are disclosed in U.S. Pat. Nos. 5,073,191 and 5,160,530 (the former being a division of the latter) of Misselbrook et al. In the process as described in those patents, a low melting agriculturally-active material, in molten form, is combined with an aqueous solution of a water-soluble film-forming polymer such as polyvinyl alcohol, at a temperature sufficient to maintain the active material in the molten state. The active material is then dispersed or emulsified in the aqueous solution and the resulting dispersion or emulsion is then spray-dried at a temperature of between approximately 50° and 220° C. so as to produce either microcapsules or microspheres containing the active ingredient. Additives such as plasticizers, wetting agents and anti-caking agents may be included in the aqueous phase for modification of the nature of the polymeric wall of the microcapsules or microspheres. The patent states that the product produced by this process is a dry, free-flowing powder or granule. However, problems occurred when the techniques of the Misselbrook et al. patents were applied in an attempt to produce microcapsules or microspheres containing the low-melting insecticide lambda-cyhalothrin, [α(S*),3α(Z)]-(±)-cyano-(3-phenoxybenzyl)-3-(2-chloro-3,3,3-trifluoro-1-propenyl)-2,2-dimethyl cyclopropane carboxylate. While the microsphere product produced by this technique appeared to be of good quality, it did not disperse well when mixed with water for spraying; because of the low melting point of the active ingredient, the material tended to melt, stick together, and plug up the spray nozzles.

The present invention, therefore, is directed to a process for production of microcapsules or microspheres containing an agriculturally active material (e.g. a molten low melting solid, a liquid active ingredient, an emulsion or a solution) which forms good quality microspheres and which disperses well in water for spraying.

SUMMARY OF THE INVENTION

This invention comprises a process for production of microspheres containing an agriculturally active material comprising the steps of (a) preparing a liquid phase comprising an agriculturally active material; (b) mixing said liquid phase with an aqueous phase comprising from about 1 to about 25 percent by weight of polyvinyl alcohol; (c) adding to this mixture of step (b) from about 5 to about 40 percent by weight, based on the mixture, of a particulate material selected from clays, silicas, water-soluble starches, starch derivatives and combinations thereof; and (d) spray-drying the resulting suspension to encapsulate the active material in polyvinyl alcohol.

This invention further comprises microspheres produced by the above process.

DETAILED DESCRIPTION OF THE INVENTION

The process of this invention is used to prepare polymeric microspheres enclosing an agriculturally active material.

In the process of this invention, the agriculturally active material, if not already in liquid form, is converted to a liquid. Liquid forms of the active material which may be used in this process include molten forms of low-melting solids, agricultural materials which are liquids at temperatures of normal use, emulsions, dispersions, and solutions in water or organic solvents.

The agriculturally active material which is enclosed within the microspheres of this invention may be either liquid or solid. Solids are first dissolved or suspended in a solvent for purposes of producing microspheres, but are contained in the final microsphere product in primarily the solid form due to evaporation of the solvent when the microspheres are formed.

Agriculturally active materials which may be used in this invention include the insecticide lambda-cyhalothrin, other pyrethroid insecticides, and herbicides such as sulfosate (trimethylsulfonium salt of N-phosphonomethylglycine, napropamide (N,N-diethyl-α-naphthoxypropionamide), trifluralin (α,α,α-trifluoro-2,6-dinitro-N,N-dipropyl-p-toluidine), paraquat (1,1'-dimethyl-4,4'-bipyridinium salts), thiocarbamate herbicides such as EPTC, butylate, and vernolate (optionally with a herbicide antidote), and the fumigant metam sodium (sodium N-methyldithiocarbamate). Sulfosate and paraquat, for instance, are water-soluble salts which are solids under normal temperatures, and which are dissolved in water for use in this invention.

In the use of the process of this invention for production of microspheres containing materials which are not water-soluble, organic and aqueous phases are prepared. For purposes of convenience, the invention will be described primarily in terms of such a two-phase system.

If an organic solvent is utilized, it is chosen on the basis of three properties. First, the solvent must dissolve the active ingredient as well as any other components of the organic phase. Secondly, the solvent preferably should have a relatively low boiling point so as to be easily removed through spray-drying. The boiling point of the solvent thus should be at a maximum of about 220° C. Thirdly, the solvent must be immiscible with water. Suitable solvents include hydrocarbons such as pentane, hexane, heptane, cyclohexane, and the like, chlorinated solvents such as dichloromethane, N-alkylpyrrolidones, gamma-butyrolactone, cyclohexanone, methylcyclohexanone, methanol, fatty acid esters and isophorone.

The organic phase will also contain an emulsifier, which may be any of a number of types known to cause emulsions to form when organic and aqueous phases are mixed. Typical emulsifiers include surfactants such as polyethylene glycol ethers of linear alcohols, ethoxylated nonylphenols, napthalenesulfonates, alkali metal/alkyl sulfates and other salts, and the like. One preferred emulsifier is the anionic/nonionic blend sold as Atlox 3409F. Other additives such as dispersants and wetting agents may be contained in either phase. Typical dispersants include naphthalene/formaldehyde condensates, lignosulfonates and naphthalene sulfonates. A preferred dispersant is Soprophor S/40P (a blend of ethoxylated tristyrylphenols). Wetting agents include naphthalene sulfonates, sulfated alkyl carboxylates and sulfosuccinates; a preferred wetting agent is Stepwet 95 (sodium lauryl sulfate).

The organic phase will typically contain from about 10 to about 95, preferably from about 30 to about 95, weight percent of the agriculturally active substance, and from about 1 to about 20, preferably from about 2 to about 4 weight percent emulsifier (if the emulsifier is present in the organic phase). If the agriculturally active substance is dissolved in a solvent, the solvent will comprise from about 10 to about 90, preferably from about 40 to about 70 weight percent of the organic phase. Dispersants, if used, will be present in from about 1 to about 20 weight percent; wetting agents, if used, in from about 0.5 to about 5 weight percent.

The aqueous phase comprises an aqueous solution of polyvinyl alcohol and optionally a buffer. It will typically contain from about 1 to about 25, preferably from about 2 to about 5 weight percent polyvinyl alcohol. If an emulsifier is used in the aqueous phase, it will comprise from about 2 to about 4 weight percent of that phase.

The organic and aqueous phases are mixed and stirred to form an emulsion. The emulsification step is conducted at a temperature of from about 10° to about 100° C., typically at ambient temperatures. If the organic phase contains an agriculturally active compound in molten form, temperature is maintained through the emulsification step sufficiently high so as to maintain that material in the molten state.

The emulsification step is carried out with stirring. The size of the microspheres ultimately formed depends to a great extent on the speed with which the emulsion is stirred. The higher the stirring speed, the smaller the droplet of active ingredient plus polymer formed in the aqueous solution. In general, to obtain the microspheres of this invention, the stirring speed should be from about 500 to about 5,000, preferably from about 500 to about 2,500 rpm. The resulting microcapsules will have a diameter of from about 3 to about 200, preferably from about 3 to about 10, microns.

To the emulsion, with stirring, is added a particulate material selected from clays, silicas, water-soluble starches and starch derivatives. Suitable clays are those which are dispersible in water and which will combine with polyvinyl alcohol to form the microspheres of this invention and include, for example, attapulgite, kaolin, montmorilonite and diatomaceous silica. Silicas useable in this invention include hydrophilic and hydrophobic precipitated or fumed silicas. Water-soluble starches and derivatives include non-pre-gelled and pre-gelled starch, maltodextrins, and cyclodextrins. One such material is methylated β-cyclodextrin, a water-soluble starch derivative, sold by Wacker-Chemie GmbH under the trademark Beta W7 M1.8. Combinations of various particulate materials may also be used.

For use in this invention, the particulate material should have a particle size of about 0.1–30 microns, needle-or plate-shaped crystals, should be non-reactive with other materials used, non-hygroscopic and should contribute to viscosity.

The particulate material is suspended in the emulsion.

The suspension containing the agriculturally active material is then converted to controlled-release microspheres by spray-drying to remove the solvent and the water. Spray-drying is carried out at an inlet temperature of from about 100 to about 300, preferably from about 150° to about 220° C. and an outlet temperature of from about 50° to about 100°, preferably from about 60° to about 75° C. The microspheres thus formed can, if desired, be further processed into other physical forms such as pellets, flakes, granules or powders.

If the agriculturally active material is a water-soluble solid or water-miscible liquid, there is no need to form a two-phase system. One may either prepare two aqueous phases and mix them, or all the ingredients including the particulate material may be combined in a simple mixing step, with stirring, to produce a suspension. Such a single mixing step is considered equivalent to, and within the terms of, the two steps defined herein as preparing a liquid phase and mixing the liquid phase with an aqueous solution containing polyvinyl alcohol.

The microcapsules of this invention demonstrate a quick release of the agriculturally active ingredient. Under microscopic examination, the microspheres formed small clusters and (compared to those of the Misselbrook et al. patents) disperse rapidly in water and do not tend to cause plugging of spray nozzles or other equipment.

The following represent examples of the preparation of microspheres according to this invention.

GENERAL PROCEDURE

An organic phase was prepared containing either molten lambda-cyhalothrin or lambda-cyhalothrin dissolved in a solvent, as indicated. An aqueous phase was prepared which contained the polyvinyl alcohol. The two phases were combined, with stirring to form an emulsion, with an emulsifying agent either having been included in the organic phase or added in the emulsification step. Then, the particulate material was added, following which the suspension was spray-dried to produce the microspheres.

The following tables show content of ingredients as starting materials and in the spray-dried microspheres. Polyvinyl alcohol was used in aqueous solutions of from 5–20% concentration; the amount of solution is indicated. Water was generally not present in the dried microspheres. Lambda-cyhalothrin was used in technical grade, 85.6% purity.

EXAMPLE 1—Using Silica

| Ingredient | Starting Amt., g. | Microsphere Content, wt. % |
| --- | --- | --- |
| lambda-cyhalothrin | 35 | 68.1 |
| dichloromethane | 27.7 | 0 |
| Atlox 3409F (emulsifier) | 5.5 | 9.7 |
| polyvinyl alcohol (5% soln.) | 100 (5) | 9.7 |
| Wessalon 50S (dispersant) | 5 | 9.7 |
| Morwet D425 (wetting agent) | 1 | 2.0 |
| Morwet EFW (wetting agent) | 0.2 | 0.4 |
| Kelzan (dispersant) | 0.2 | 0.4 |

EXAMPLE 2—Using Molten lambda-cyhalothrin

| Ingredient | Starting Amt., g. | Microsphere Content, wt. % |
|---|---|---|
| lambda-cyhalothrin (molten) | 47.9 | 47.9 |
| polyvinyl alcohol (8% soln.) | 125 (10) | 10 |
| Atlox 3409F | 6.5 | 6.5 |
| Huber 95 (kaolin clay) | 29.6 | 29.5 |
| Soprophor 5/40P | 5 | |
| Stepwet 95 | 1 | 1 |

EXAMPLE 3—Using beta-cyclodextrin

| Ingredient | Starting Amt., g. | Microsphere Content, wt. % |
|---|---|---|
| lambda-cyhalothrin | 30 | 30 |
| polyvinyl alcohol (20% soln.) | 40 (8) | 8 |
| Beta W7 M1.8 | 46 | 46 |
| Atlox 3409F | 8 | 8 |
| Aromatic 200 solvent | 8 | 8 |

EXAMPLE 4

| Ingredient | Microsphere Content, wt. % |
|---|---|
| lambda-cyhalothrin | 47 |
| polyvinyl alcohol | 8 |
| Atlox 3409F | 9 |
| Soprophor S/40P | 8 |
| Stepwet 95 | 1 |
| Attagel 50 (attapulgite clay) | 19 |
| methyl caprylate/caurate (solvent) | 8 |
| phosphoric buffer | 0.07 |

What is claimed:

1. A process for production of microspheres containing an agricultural pesticide comprising the steps of
    (a) preparing a liquid phase comprising a liquid agricultural pesticide, said liquid phase being in the form of a molten low melting solid, a liquid active pesticidally active ingredient, an emulsion, or a solution of a liquid or solid pesticide in a solvent;
    (b) mixing the liquid phase with an aqueous phase comprising from about 1 to about 25 percent by weight of polyvinyl alcohol;
    (c) adding to the mixture of step (b) from about 5 to about 40 percent by weight, of a particulate material selected from clays and silicas; and
    (d) spray drying the resulting suspension to encapsulate the active agricultural pesticide.

2. A process according to claim 1 in which the agricultural pesticide is dissolved in an organic solvent in the liquid phase.

3. A process according to claim 1 in which the agricultural pesticide is present in molten form in the liquid phase.

4. A process according to claim 1 in which the agricultural pesticide is a water-soluble solid and the liquid phase comprises an aqueous solution of the solid.

5. A process according to claims 2 or 3 in which either the liquid phase or the aqueous phase further contains a dispersant.

6. A process according to claims 2 or 3 in which either the liquid phase or the aqueous phase further contains a wetting agent.

7. A process according to claims 2 or 3 in which the liquid phase is emulsified in the aqueous phase.

8. A process according to claim 7 in which the emulsification is carried out at a temperature of from about 10° to about 100° C.

9. A process according to claim 1 in which the liquid phase contains from about 10 to about 95 weight percent of the agricultural pesticide.

10. A process according to claim 1 in which the liquid phase contains from about 70 to about 85 weight percent of the agricultural pesticide.

11. A process according to claim 7 in which the emulsification step is carried out under a stirring speed of from about 500 to about 5,000 rpm.

12. A process according to claim 1 in which the agricultural pesticide comprises lambda-cyhalothrin.

13. A process according to claim 12 in which the lambda-cyhalothrin is present in the liquid phase in the molten state.

14. A process according to claim 1 in which the agricultural pesticide comprises sulfosate.

15. Microspheres containing an agricultural pesticide produced by the process according to claim 1.

16. Microspheres containing an agricultural pesticide produced by the process according to claim 2.

17. Microspheres containing an agricultural pesticide produced by the process of claim 3.

18. Microspheres containing an agricultural pesticide produced by the process of claim 4.

19. A process according to claim 1 in which the pesticide is a low-melting solid.

20. A process according to claim 1 in which the particulate material is added in step
    (c) in an amount of from about 14 to about 40 percent by weight.

* * * * *